(12) United States Patent
Brooks et al.

(10) Patent No.: US 6,520,912 B1
(45) Date of Patent: Feb. 18, 2003

(54) METHOD AND SYSTEM FOR DISPLAYING MEDICAL DATA SUCH AS A DIAGNOSTIC MEDICAL ULTRASOUND IMAGE AT AN AUTOMATICALLY-SELECTED DISPLAY RESOLUTION

(75) Inventors: Mark A. Brooks, Gregory, MI (US); Adam D. Marks, Howell, MI (US); Huijia Jin, Troy, MI (US); David R. Hall, Ann Arbor, MI (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/710,762

(22) Filed: Nov. 9, 2000

(51) Int. Cl.[7] .................................................. A61B 8/00
(52) U.S. Cl. ...................................................... 600/437
(58) Field of Search ................................ 600/437, 407, 600/440–447, 479, 546; 382/107, 132; 705/1–3; 345/419, 427–8, 536, 699, 660

(56) References Cited

U.S. PATENT DOCUMENTS

| | | | |
|---|---|---|---|
| 4,833,625 A | * | 5/1989 | Fisher et al. ................. 345/536 |
| 5,235,510 A | * | 8/1993 | Yamada et al. .............. 128/922 |
| 5,416,602 A | * | 5/1995 | Inga et al. ................ 358/261.1 |
| 5,542,003 A | * | 7/1996 | Wofford ....................... 345/660 |
| 5,612,715 A | | 3/1997 | Karaki et al. |
| 5,776,073 A | * | 7/1998 | Garfield et al. .............. 600/546 |
| 5,982,373 A | | 11/1999 | Inman et al. |
| 6,260,021 B1 | * | 7/2001 | Wong et al. .................... 705/1 |
| 6,295,048 B1 | * | 9/2001 | Ward et al. .................. 345/699 |

FOREIGN PATENT DOCUMENTS

| JP | 410069265 A | * | 3/1998 | ............ G09G/5/00 |
|---|---|---|---|---|

* cited by examiner

Primary Examiner—Marvin M. Lateef
Assistant Examiner—Ali M. Imam (57) ABSTRACT

The preferred embodiments described herein provide a method and system for displaying medical data at an automatically-selected display resolution. In one preferred embodiment, medical data is automatically analyzed, and based on the analysis, a display resolution is automatically selected. The medical data is then displayed with the automatically-selected display resolution. By automatically selecting a display resolution based on an analysis of medical data, the appearance of medical data is optimized without conscious effort by a user. Other preferred embodiments are provided.

28 Claims, 6 Drawing Sheets

MAJOR CARDIOLOGY HOSPITAL
Echocardiography Laboratory
Telephone: (555) 555-1234  Fax: (555) 555-5678

ECHO REPORT

| | | | |
|---|---|---|---|
| Patient Name: | Jon Wierer | Patient ID: | 4550899 |
| Exam Date: | October 27, 2000 | Patient Age: | 51 |
| Date of Report: | October 28, 2000 | Height: | 182 cm |
| Referring Phys: | Lisa Ward | Weight: | 55 kg |

Measurements

| | |
|---|---|
| LVDD: | 5.4 cm |
| LVSD: | 4.4 cm |
| Fract. Short. | 33% |
| Aortic Valve: | 1.1 cm |

Diagnosis

Patient is at low risk of heart disease.

The left ventricular chamber is normal in size.

Mindy McDaniel, M.D.

METHOD AND SYSTEM FOR DISPLAYING MEDICAL DATA SUCH AS A DIAGNOSTIC MEDICAL ULTRASOUND IMAGE AT AN AUTOMATICALLY-SELECTED DISPLAY RESOLUTION

BACKGROUND

Medical data (such as a medical diagnostic ultrasound image) can be generated by a diagnostic medical image acquisition device (such as an ultrasound imaging system), stored in digital form, and displayed on a diagnostic medical data review system (such as a computer). In addition to displaying the medical image, the review system can also execute medical reporting software that allows a reading physician or other clinical user to create an electronic medical report. A review system typically comprises a display subsystem, such as a graphics card and monitor, that is responsible for displaying medical data to a user. The review system is usually programmed to display medical data at a specific display resolution. While this display resolution may be preferred for some applications, it may not be desired when displaying some medical data. To address this problem, some review systems allow a user to explicitly configure the display subsystem to display medical data at a user-specified display resolution. However, physicians and other clinical users may not have the experience or the time to manually adjust the display resolution of the review system. Accordingly, medical data is often sub-optimally displayed.

There is a need, therefore, for a method and system for displaying medical data at an automatically-selected display resolution.

SUMMARY

The present invention is defined by the following claims, and nothing in this section should be taken as a limitation on those claims.

By way of introduction, the preferred embodiments described below provide a method and system for displaying medical data at an automatically-selected display resolution. In one preferred embodiment, medical data is automatically analyzed, and based on the analysis, a display resolution is automatically selected. The medical data is then displayed with the automatically-selected display resolution. By automatically selecting a display resolution based on an analysis of medical data, the appearance of medical data is optimized without conscious effort by a user. Other preferred embodiments are provided.

The preferred embodiments will now be described with reference to the attached drawings.

DETAILED DESCRIPTION OF THE PRESENTLY PREFERRED EMBODIMENTS

Figure 1:
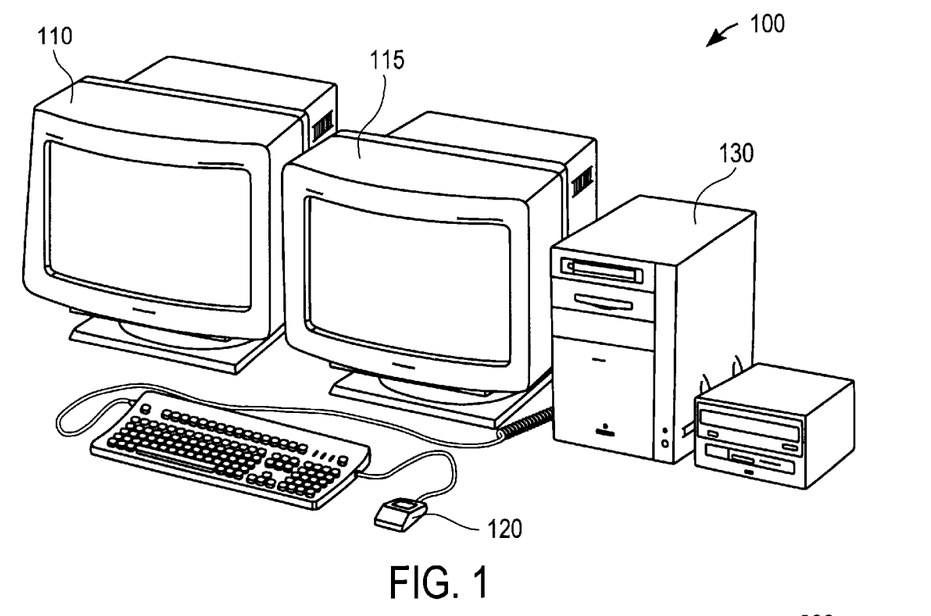
FIG. 1 is an illustration of a diagnostic medical data review system of a preferred embodiment.

Turning now to the drawings, FIG. 1 is an illustration of a diagnostic medical data review system 100 of a presently preferred embodiment. The diagnostic medical data review system 100 of this preferred embodiment comprises a first and second display device 110, 115, a mouse 120, and a processor 130. Although two display devices are shown in FIG. 1, the medical data review system 100 can have only one display device or can have three or more display devices. When multiple display devices are used, the processor 130 can be configured to treat the multiple display devices as if they were a single display device (i.e., each separate display device presents only part of a single display output). The processor 130, which is coupled with the display devices 110, 115 and mouse 120, is operative to display, review, and analyze stored or retrieved diagnostic medical data. As used herein, the term "coupled with" means directly coupled with or indirectly coupled with through one or more components. It is presently preferred that the review system be a part of the KinetDx™ system available from Acuson Corporation of Mountain View, Calif.

As used herein, the term "medical data" broadly refers to a medical image (e.g., still or moving) and/or a medical report. As also used herein, the term "medical report" broadly refers to any non-image medical data, such as a worksheet or a textual and/or graphical presentation of information such as patient demographics, measurements, comments, and/or diagnoses. In this preferred embodiment, the processor 130 is operative to automatically analyze medical data, automatically select a display resolution for the medical data based on the analysis, and display the medical data on the display device 110, 115 with the automatically-selected display resolution. As used herein, the term "processor" broadly refers to the appropriate hardware and/or software components of the review system 100 that can be used to implement this functionality and the functionality described below. The processor can also implement other functionality. It should be understood that any appropriate hardware (analog or digital) or software can be used and that the embodiments described herein can be implemented exclusively with hardware. Further, the processor 130 can be separate from or combined with (in part or in whole) other processors of the review system 100 (including attendant processors). Also, the processor 130 can comprise several components, and the functionality described herein can be distributed among these components.

Figure 2:
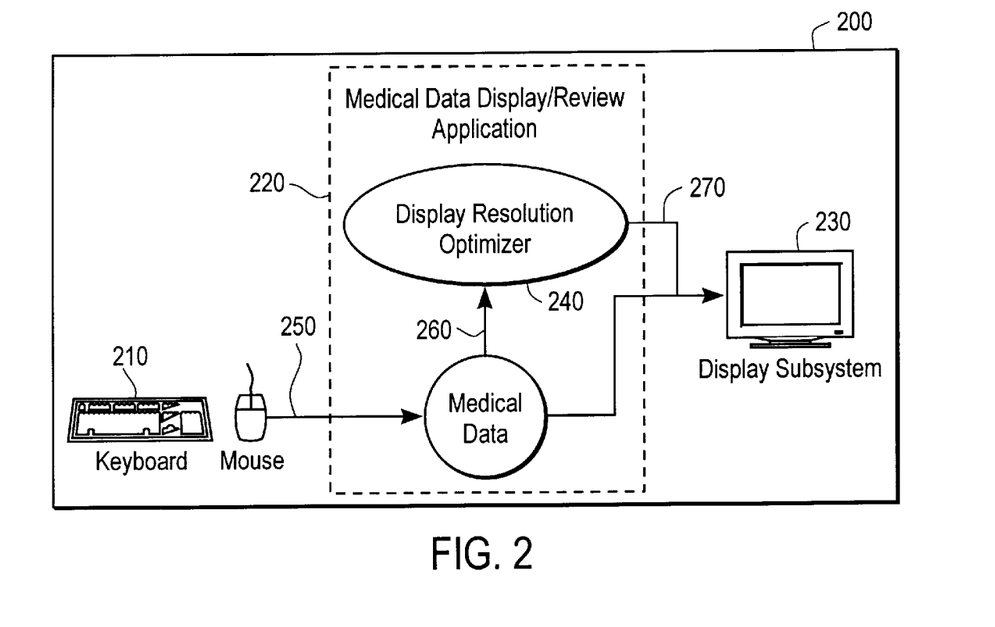
FIG. 2 is a block diagram of a diagnostic medical data review system of a preferred embodiment.

FIG. 2 is one preferred implementation of the hardware and/or software components (i.e., of the "processor"). The review station 200 shown in FIG. 2 comprises user interface elements 210 (e.g., a keyboard and a mouse), a medical data display/review application 220, and a display subsystem 230. The review station 200 can comprise additional components, which are not shown in FIG. 2 for clarity. The display subsystem 230 in this preferred embodiment comprises a graphics card and/or graphics processor and a display device (such as a monitor or projector) on which the graphics card displays its output. The review station 200 supports a plurality of display resolutions, and the display subsystem is configured to display a subset (e.g., one) of these display resolutions. As used herein, "display resolution" generally describes the pixel density employed by the display subsystem 230. For example, with a display resolution of 1024 by 768, the display subsystem 230 displays a grid of pixels consisting of 1024 columns and 768 rows.

In this preferred embodiment, the medical data display/review application 220 comprises a display resolution optimizer 240 that analyzes medical data and dynamically adjusts or selects the resolution used by the display subsystem 230 so that the medical data is optimally displayed. The display resolution that is considered "optimal" is the resolution at which medical data is displayed to achieve a desired result. In one preferred embodiment, medical data is optimally displayed when at least a portion of the medical data best fits a criterion. As used herein, a "best fit" means either the best fit itself (e.g., a largest image) or based on a best fit (e.g., the second largest image). For example, when displaying images, the optimal resolution can be the resolution that results in the largest number of images being displayed, or it can be the resolution that results in images being displayed as large as possible. The optimal resolution can also be the resolution that results in a medical image being as large as possible without looking distorted when viewed at a comfortable viewing distance (e.g., no more than two-times its original size). When displaying medical reports, the optimal display resolution can be the resolution at which textual displays render specific fonts in the most aesthetic manner. Also, dynamically adjusting the display resolution can allow a user to view medical data without excessive eye movement or eye strain. In other words, the display resolution can be automatically selected to place the medical data into a user's visual comfort zone, which can be determined by the combination of the user's field of vision and the distance between the user and the monitor.

In operation, an interaction with the medical data display/review application 220 results in the application 220 displaying medical data using the display subsystem 230. The interaction can be the result of a user interacting with the system using user interface elements 210 (as shown in act 250) or the result of another program or computer system. For example, a user can open medical data stored in a server separate from or integrated with the review station or stored on a portable storage medium (such as a magneto-optical disk). The selection of an image presentation mode can trigger the use of the display resolution optimizer 240. Before or after the medical data is displayed on the display device, the medical data is sent to the display resolution optimizer 240 (act 260). The display resolution optimizer 240 analyzes the medical data and, based on the analysis, automatically selects a display resolution. The display subsystem 230 is then configured to use the selected display resolution (act 270). This configuration can be performed by the display resolution optimizer 240 itself or by the application program employing it. The medical data is then displayed on the display device using the automatically-selected display resolution.

There are several advantages associated with these preferred embodiments. By automatically selecting the display resolution based on the medical data being displayed, the appearance of medical data is optimally displayed (i.e., achieves a desired end result). Further, because the selection of the display resolution is an automated process, the user does not have to put forth a conscious effort to select an optimal display resolution. This can be especially important for physicians and other clinical users who may not have the experience or the time to manually adjust the display resolution. The ability to dynamically change resolutions based on the type of data being displayed results in the ability to switch between the display system's default resolution and alternate resolutions that are preferred for the type of data being displayed.

Figure 3:
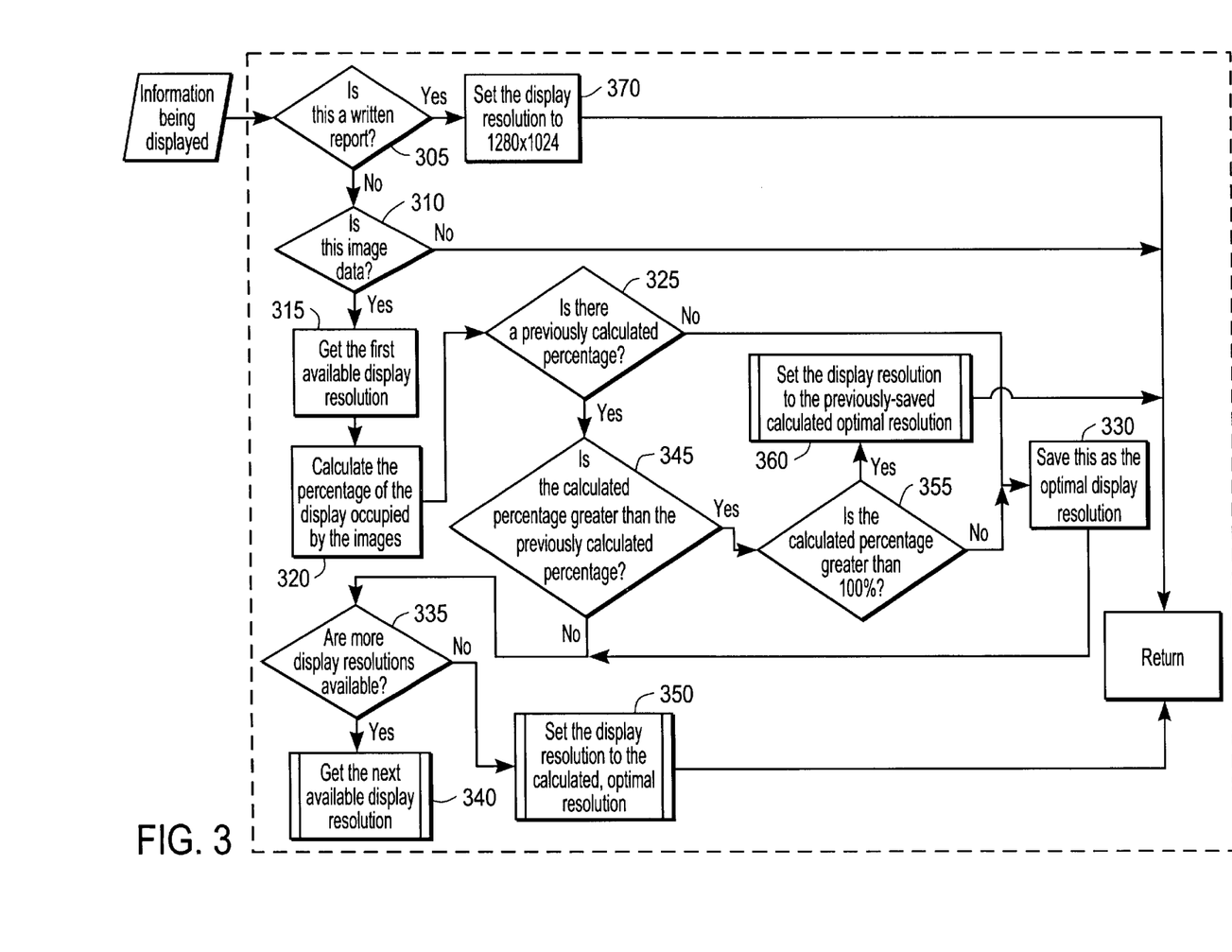
FIG. 3 is a flow chart of a method of a preferred embodiment for automatically analyzing medical data and automatically selecting a display resolution based on that analysis.

Turning again to the drawings, FIG. 3 is a flow chart illustrating a method of a preferred embodiment for analyzing medical data and selecting a display resolution based on that analysis. As stated above, one way in which to analyze medical data is to compare at least a portion of the medical data to a criterion. In this preferred embodiment, the information being displayed is first analyzed to determine if it is a written report (act 305) or a medical image (act 310). If the information is neither a medical report nor a medical image, a preset display resolution is used to display the information.

Figure 4A:
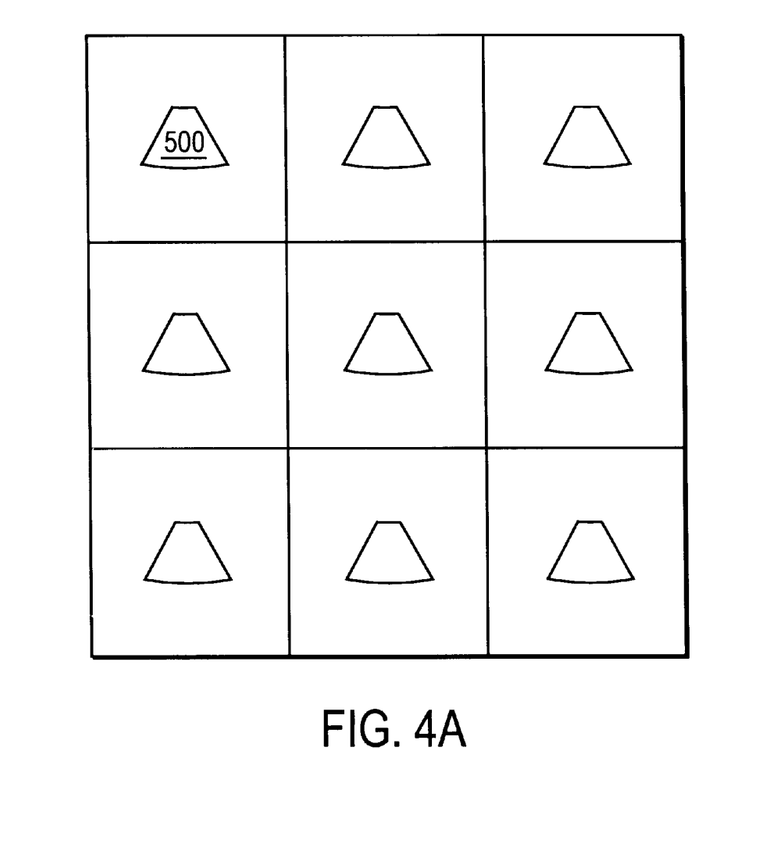
FIGS. 4A and 4B are illustrations of displayed medical images in a "9-up" film style of a preferred embodiment.

To illustrate this preferred method, a review system capable of displaying data at a plurality of resolutions (1280 by 1024, 1024 by 768, and 640 by 480) will be described. Further, the review system will be used to display medical images in a "9-up" film style. As shown in FIG. 4A, in a "9-up" film style, medical images are organized into a two-dimensional grid that is three images wide and three images tall. It should be noted that other image layouts can be used, such as "4-up" and "16-up." In this preferred embodiment, each of the displayed images has the same size: 320 by 240. Accordingly, the analysis will be performed on only one of the images (image 500). If the images are not the same size, an image of the most common size or an image based on some other characteristic (e.g., the most important image) can be automatically selected. Alternatively, the user can manually select the image that will be automatically analyzed.

Figure 5A:
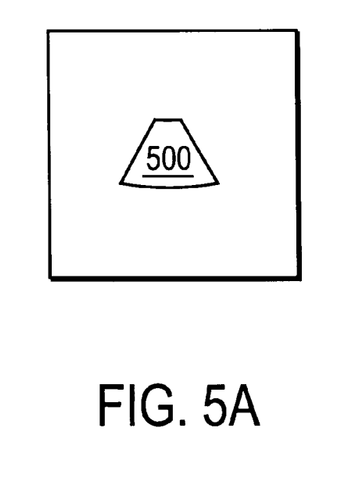
FIGS. 5A, 5B, and 5C are illustrations of medical images illustrating the operation of the preferred method shown in the flow chart of FIG. 3.

In this preferred embodiment, the display resolution optimizer 240 analyzes the medical images at each of the available display resolutions and selects the display resolution that best fits the criterion of images occupying the largest percentage of their respective grid locations (i.e., the largest occupied screen area). Turning back to the flow chart of FIG. 3, the first available display resolution is selected (act 315), and the percentage of the display occupied by the images is calculated (act 320). Figure 5A is an illustration of a medical image 500 displayed in one of the nine grid locations at a resolution of 1280 by 1024. At this resolution, the medical image occupies about 53% of its grid location. It should be noted that other displayed information, such as a menu bar, can be taken into account when determining the percentage of the display occupied by the medical images. It is then determined whether there is a previously-calculated percentage (act 325). Since this is the first resolution that is tested, there is not a previously-calculated percentage, and the resolution of 1280 by 1024 is saved as the optimal display resolution (act 330). At act 335, it is determined that there are more display resolutions available. The next available display resolution is chosen at act 340, and the above-analysis is carried out on the images with the newly-chosen display resolution.

Figure 5B:
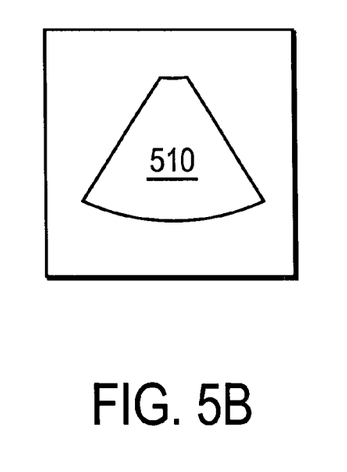

As illustrated in FIG. 5B, the medical image 510 occupies about 88% of its grid location at the display resolution of 1024 by 768. Because there is a previously-calculated percentage (see act 325), the current calculated percentage (88%) is compared with the previously-calculated percentage (53%) to see which percentage is larger (act 345). Since the current calculated percentage is larger, it is then determined whether the current calculated percentage is greater than 100% (act 355). In this case, the current calculated percentage is not greater than 100%, and the resolution of 1024 by 768 is saved as the optimal display resolution (act 330).

Figure 4B:
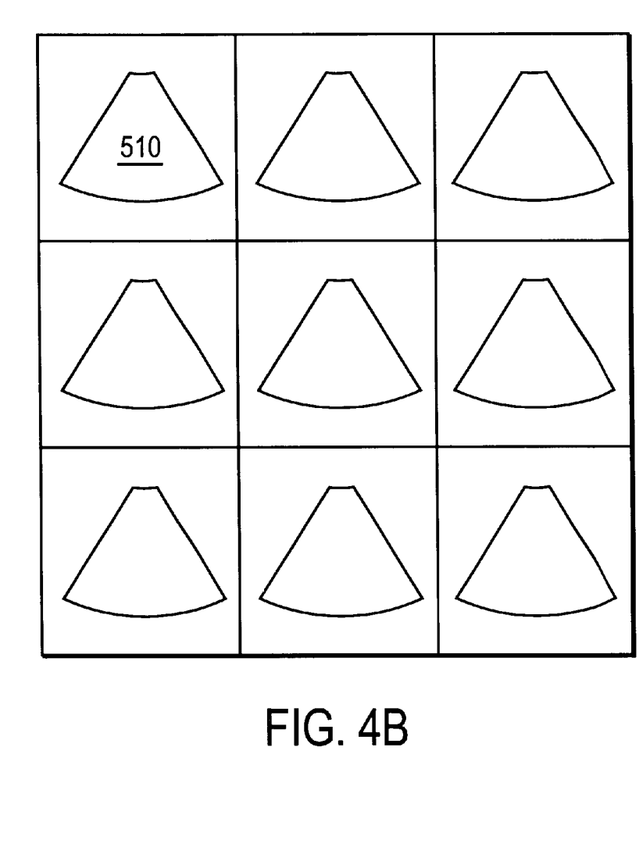
Figure 5C:
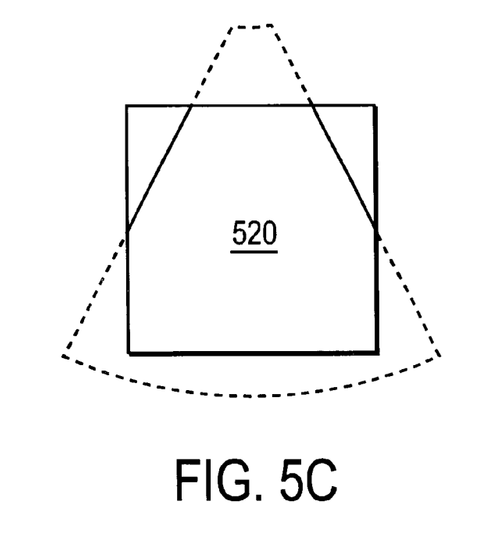

It is again determined whether there are any remaining display resolutions available (act 335). If there are no more display resolutions available, the display resolution is set to the saved calculated, optimal resolution (act 350). In this example, there is one remaining display resolution (640 by 480), and the analysis described above is performed on the image using this display resolution. The medical image 520 occupies about 225% of its grid location at this display resolution, causing the image 520 to be larger than the grid location assigned to it, as illustrated in FIG. 5C. Because the calculated percentage is greater than 100% (see act 355), the display resolution is set to the previously-saved calculated optimal resolution (act 360), which in this example is 1024 by 768. The medical images are then displayed at this resolution. As shown in FIG. 4B, at a display resolution of 1024 by 768, the medical images almost entirely fill the display grids in both the horizontal and vertical dimensions.

Figure 6:
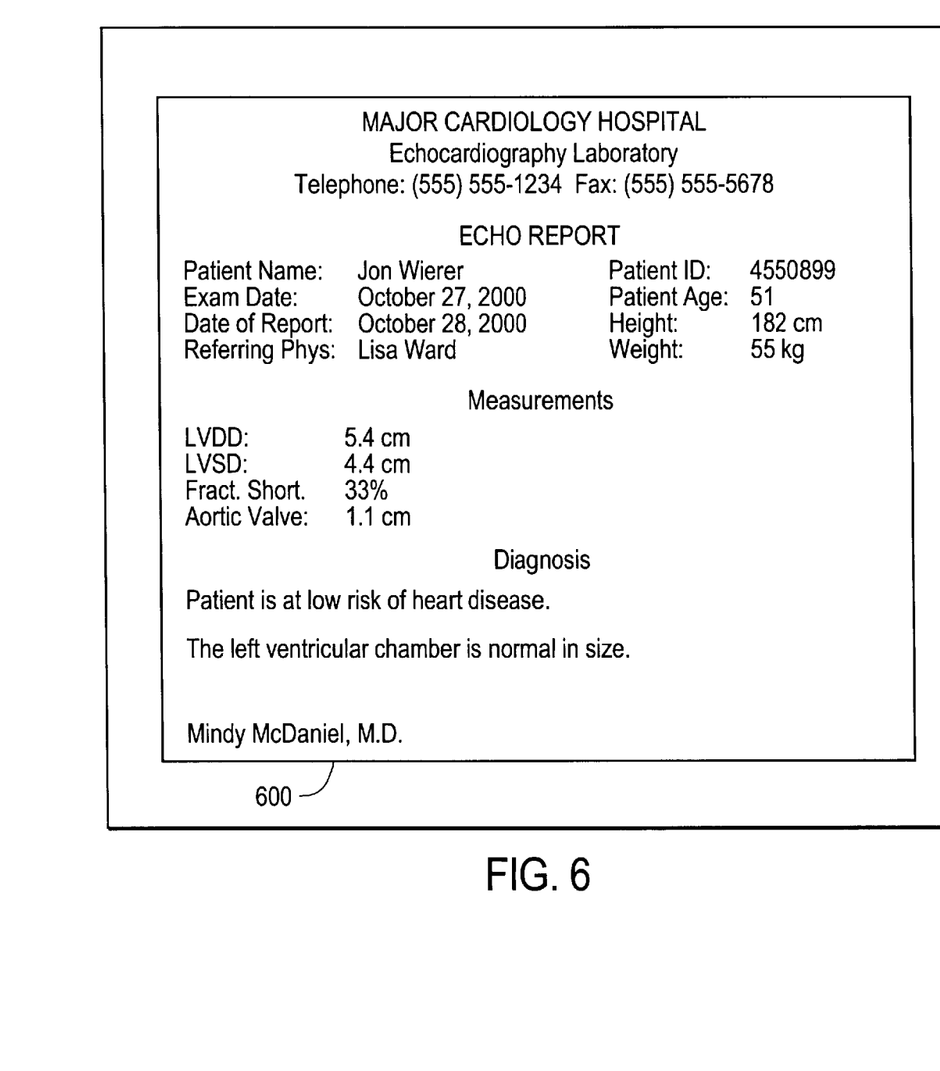
FIG. 6 is an illustration of a displayed medical report of a preferred embodiment.

In addition to medical images, a medical report can also be displayed. In this example, the medical report would not display well at the display resolution automatically selected for medical images (1024 by 768) because the text of the report would look grainy, and there would be problems with line-wrapping. Accordingly, this method preferably differentiates between medical images and medical reports at act 305 in the analysis. When the information to be displayed is a medical report, the display resolution is automatically adjusted to 1280 by 1024 (act 370)—a resolution predetermined to be aesthetically-pleasing to a user. In this way, the report 600 is displayed in an aesthetically pleasing manner (see FIG. 6). If medical images are later display, the display resolution optimizer 240 is again employed to analyze the information being displayed. Based on this analysis, the display resolution optimizer 240 determines the optimal resolution and triggers a resolution change. For example, if a user closes the medical report 600 to once again display the 9-up images in FIG. 4B, the display resolution optimizer 240 automatically changes the display resolution back to 1024 by 768.

Figure 7:
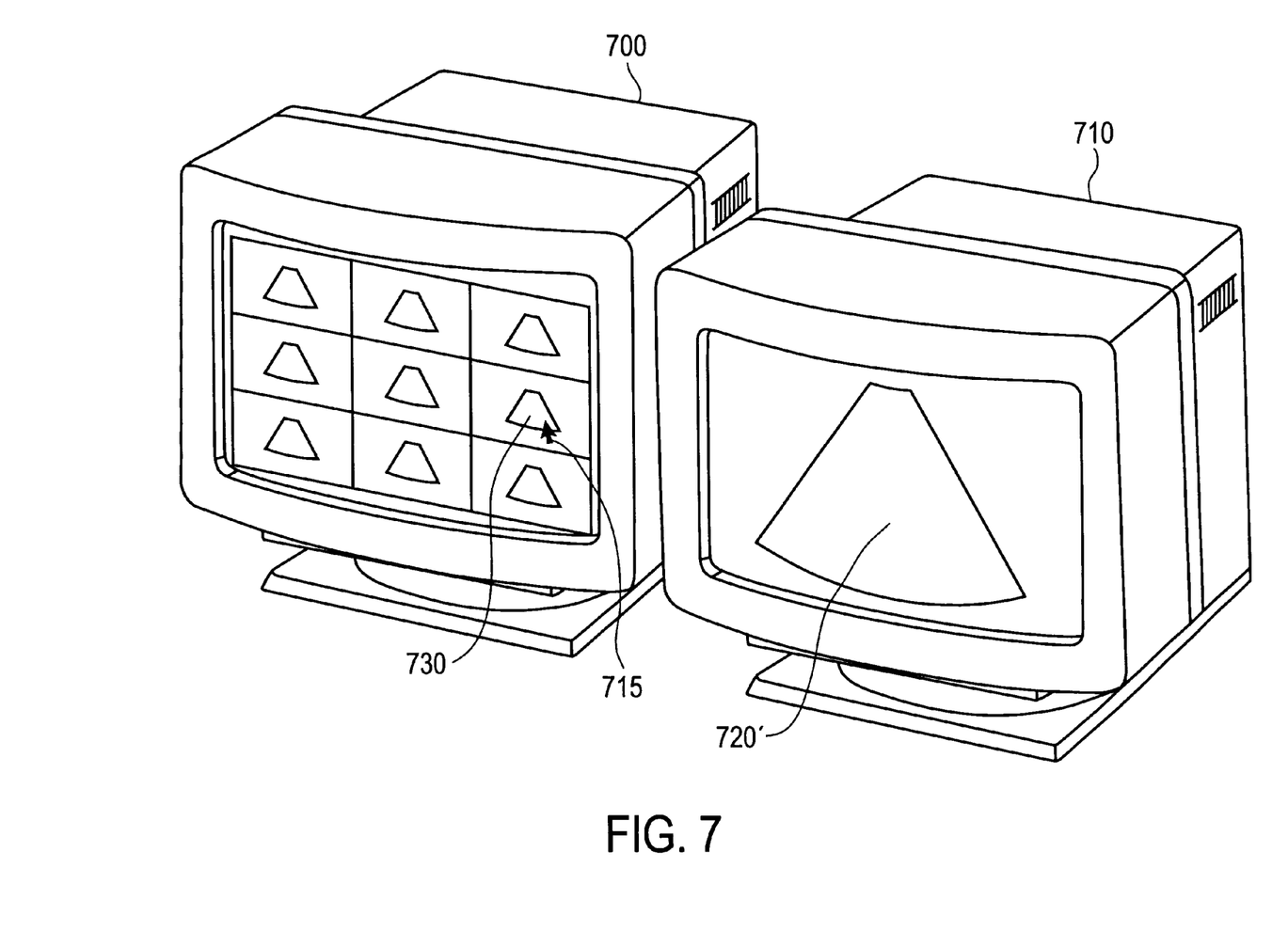
FIG. 7 is an illustration of a presentation mode of a preferred embodiment.

In addition to the advantages described above, one additional advantage of these preferred embodiments is that it allows for new techniques for displaying and presenting images. One such new technique, which will be referred to as a "presentation mode," is illustrated in FIG. 7. In the presentation mode, two display devices 700, 710 are used. The first display device 700 displays a plurality of images, and the second display device 710 displays one of the plurality of images from the first display device 700. The image displayed on the second display device 710 can be manually selected by a user (using an on-screen pointer 715, for example) or can be automatically selected. The selected image is automatically analyzed, and a display resolution is automatically selected, as described above. The automatically-selected display resolution is used to display the image on the second display device. One application for the presentation mode is in a teaching setting, where an instructor wishes to get a quick snap shot of available images and select an image to present to one or more students. The instructor also wishes the selected image to be displayed as large as possible on the second display device 710 so that his students can easily see the selected image. In operation, the first display device 700 displays a plurality of available images ("navigation images") at a predetermined or automatically-selected resolution, and the instructor then selects an image 720 from these navigation images. The review system then automatically analyzes the selected image 720 and automatically selects a display resolution that will result in the image 720 appearing as large as possible on the second display device 710. The review station then displays the image 720' at the automatically-selected display resolution. Because two display devices are used, the second display device 710 can be positioned in a different direction from the first display device 700, thereby facilitating the presentation of the image of interest to students. When the second display device takes the form of a projector, the image of interest can be projected to further facilitate the presentation.

There are several alternatives that can be employed with these preferred embodiments. In the example illustrated above, the medical data was analyzed to determine which display resolution resulted in the images occupying the largest percentage of their respective grid locations. Other criterion can be used. For example, in another preferred embodiment, a display resolution is automatically selected to fit as many images as possible onto the monitor. In yet another preferred embodiment, the display resolution is automatically selected so that the image is displayed at the resolution at which it was acquired (i.e., displayed at its full, 1× scale). Further, the criterion used in the analysis of medical data can be dependent upon image layout. For example, a display resolution can be chosen to display the largest image if a 4-up image layout is used, or a display resolution can be chosen to display the smallest image if a 9-up image layout is used. As illustrated by this example, the display resolution optimizer 240 can employ any number of optimization algorithms. Additionally, it should be noted that the display resolution can be selected before the medical data is displayed or after the medical data is displayed. In the later situation, the medical data would be displayed with a first display resolution. The display resolution would then be adjusted to a second display resolution, and the medical data would be re-displayed at the second display resolution.

As another alternative, a portion of the medical data is analyzed with respect to a criterion. For example, a button displayed on a medical image can be compared to a button having a size that allows for easy selection by a user. The display resolution can be automatically selected such that the size of the displayed button best fits the size of the criterion button. As another example, the display resolution can be automatically selected so that a medical image is large enough for a user to easily interact with the image using a screen tool, such as a caliper.

In another alternative embodiment, the medical data is associated with an identifier, and a display resolution that is associated with the identifier is automatically selected. For example, different diagnostic medical image acquisition device manufacturers use different medical image formats. Viewing medical images generated by different diagnostic medical image acquisition device manufacturers can result in images of an undesired size or in a presentation of non-uniform image sizes. With these preferred embodiments, the medical images can be analyzed to determine the diagnostic medical image acquisition device manufacturer associated with the image, and a display resolution associated with that diagnostic medical image acquisition device manufacturer can automatically be selected. For example, a look-up table can be created where each diagnostic medical image acquisition device manufacturer is associated with a display resolution that will result in its images being the same (or close to the same) size as the other displayed images.

Additionally, it should be noted that some review systems may not be capable of implementing a display resolution that will provide the desired result. For example, a medical data review system may not be able to implement a display resolution that will allow a medical image to be reduced to a desired level. (The highest display resolution of many current review systems is 1600 by 1200, and the desired level may require a higher resolution.) In this situation, the medical data can be scaled (e.g., ¼×, ⅕×, ⅙×) to a size that will render the medical data to a size suitable for manipulation by display resolution changes. Further, while a medical data review station was used to illustrate the preferred embodiments described above, it should be understood that the methods described above can be implemented on any device capable of displaying medical data. Accordingly, these techniques can be used with a medical data review system, a medical data acquisition device (such as a medical diagnostic ultrasound imaging system), or a general-purpose computer. Further, it should be noted that any of the various aspects of any of the preferred embodiments can be used alone or in combination.

Finally, it should be noted that any medical data can be used with these preferred embodiments. Medical data can generated by or used in conjunction with any of the following imaging modalities: computed radiography, magnetic resonance, angioscopy, color flow Doppler, cystoscopy, diaphanography, echocardiography, fluoresosin angiography, laparoscopy, magnetic resonance angiography, positron emission tomography, single-photon emission computed tomography, x-ray angiography, computed tomography, nuclear medicine, biomagnetic imaging, culposcopy, duplex Doppler, digital microscopy, endoscopy, fundoscopy, laser surface scan, magnetic resonance spectroscopy, radiographic imaging, thermography, and radio fluroscopy. Further, a diagnostic medical image acquisition device can comprise any suitable component for generating diagnostic medical data. For example, for ultrasound images, the acquisition device can take the form of a diagnostic medical ultrasound imaging system, in which a processor causes a transmit beamformer to apply a voltage to a transducer to cause it to vibrate and emit an ultrasonic beam into the patient's body/tissue. Ultrasonic energy reflected from the body impinges on the transducer, and the resulting voltages created by the transducer are received by a receive beamformer. The processor processes the sensed voltages to create an ultrasound image associated with the reflected signals and displays the image on a display device. The processor can also store the generated image and other non-image data in a local storage device such as a hard drive.

In one preferred implementation, the review system comprises a Pentium processor using a Windows NT operating system, a Matrox Millenium G200 SD graphics card with 8 Mb of ram, and a Barco MWD 321 PLUS monitor. The review system also comprises a graphics card that implements the multiple-moving-image functionality described in U.S. patent application Ser. No. 09/200,170 ("Method and System for Simultaneously Displaying Diagnostic Medical Ultrasound Image Clips"), which is assigned to the assignee of the present application and is hereby incorporated by reference. Appendix 1 is C++ source code of a preferred embodiment to dynamically optimize the display resolution based on the information being displayed.

It is intended that the foregoing detailed description be understood as an illustration of selected forms that the invention can take and not as a definition of the invention. It is only the following claims, including all equivalents, that are intended to define the scope of this invention.

APPENDIX 1

```
//////////////////////////
// METHOD NAME:
// determineDisplayUtilization
//
// DESCRIPTION:
// Return the percentage of the grid cell occupied by the
    image
// as a number between zero and one. The algorithm calcu-
    lates
// the precentage by choosing the largest image scale factor
    that
// allows the image to be entirely displayed within the
    confines
// of the grid cell.
//
// INPUTS:
// in Grid Cell Size-
// The size of the grid cell that the image is
// constrained to.
// inImage-
// The image to be displayed within the grid cell.
//

Float 64
DisplayResolutionOptimizer::::determineDisplay
    Utilization(
    const SizeInPixels& inGridCellSize,
    const Pointer<Abstract::ImageInterface>& inImage)
{
SizeInPixelslargestSize (0, 0);
//
// Starting with the smallest scale factor and working to
    the
// largest, find the scale factor that is as large as possible
// yet still allows the entire image to fit within the grid cell.
for                                                    (UInt32
    i=Abstract::ImageScaleFactor::kSmallestScaleFactor;
    i<Abstract::ImageScaleFactor::kLastScaleFactor;
    i++)
{
//
// Determine the size of the image at the given scale factor.
//
SizeInPixels imageSize=inImage->sizeIfScaledBy (
//
    static₁₃cast<Abstract::ImageScaleFactor::Enum>(i));
if (imageSize>inGridCellSize)
{
    //
    // The image is scaled to a size where it no longer
    // will fit into the grid cell. Break out of the loop.
    //
    break;
}// if
//
// Save the size of the scaled image. At present, this is the
// largest size where the entire image fits entirely within
    the
// grid cell.
largestSize=imageSize;
}// for
//
```

```
// Return the percentage of the grid cell occupied by the
    image
as a number between zero and one.
return (
    static_13cast<Float64>(largestSize.width( ) *
        largestSize.height( ))/
    static_13cast<Float64>(inGridCellSize.width( ) *
        inGridCellSize.height( )));
}
///////////////////////////
// METHOD NAME:
// selectOptimalDisplayLayout
//
// DESCRIPTION:
// This function examines the information that is being
    displayed and
// sets the display resolution so that the information is
    displayed
// in an optimal fashion.
// INPUTS:
// inConfiguration -
// The configuration object contains all of the information
    describing
// what is being displayed and how it is organized on the
    display.
//
//
    void
    DisplayResolutionOptimizer::se-
        lectOptimalDisplayLayout (
        WorkflowRadiology::DisplayConfiguration&
            inConfiguration)
    {
        if (inConfiguration.doesConfiguredDisplayTextReport(
            ))
        {
            //
            // A report is being displayed. The optimal resolution
            // for reports is 1280×1024. Set the display resolution
            // and return.
            //
            inConfiguration.setDisplayResolution (
                inConfiguration.getDisplayResolution (k1280×
                    1024));
            return;
        }// if
        //
        // A report is not being displayed, therefore images are.
        // Select the optimal display resolution based on the
            images
        // being displayed.
        //
        //
        // Retrieve an iterator over all of the available display
        // resolutions.
        //
        WorkflowRadiology::AvailableDisplayResolutions
            availableResolutions=
            inConfiguration.getAvailableDisplayResolutions( );
        //
        // Retrieve the image series that is going to be dis-
            played.
        // Determine the most frequently occurring image size.
            This
        // will be the size that we optimize the display for.
        //
        // Pointer<MetaImageSeries>imageSeries=NEW
            MetaImageSeries (
            inConfiguration.getImageSeries(studyId( )));
        Pointer<Abstract::ImageInterface>image=
            imageSeries->staticImageWithMostFrequentSize( );
        // By default we will identify the first resolution in the
            list
        // as the optimal display resolution.
        //
        DisplayResolution optimalResolution=
            availableResolutions.DisplayResolution( );
        Float64 optimalUtilization=0.0;
        //
        // Iterate through each display resolution in the list.
        // Select the optimal resolution by choosing the one in
            which
        the images occupy the largest percentage of the display.
        //
        while (availableResolutions.remainingDisplay
            ResolutionsInclusive( ) !=0)
        {
            // Construct a grid layout manager that organizes the
                display
            // into grid having "m" columns and "n" rows. Each
                cell
            // within the grid will contain a single image. The
                size
            // of the cell determines the amount of screen real-
                estate
            // available for the image.
            //
            //       GridLayoutManager        grid=
                constructLayoutManager
                (availableResolutions.displayResolution( ),
                inConfiguration.gridWidthAndHeight( ));
            SizeInPixels            gridCellSize=
                grid.maximumAvailableComponentSpace( );
            //
            // Determine what percentage of the cell area is
                occupied
            // by the image.
            //
            // Float64 utilization=determineDisplayUtilization
                (gridCellSize, image);
            //
            // If a larger percentage of the cell area is occupied,
            // then we are making more efficient use of the
            // screen real-estate. This display resolution is more
            // optimal than the previous one.
            //
            // if (utilization>optimalUtilization)
            {
                optimalUtilization=utilization;
                optimalResolution=
                    availableResolutions.displayResolution( );
            }// if
            availableResolutions.nextDisplayResolution( );
        }// while
        inConfiguration.setDisplayResolution
            (optimalResolution);
    }
```

What is claimed is:

1. A method for displaying medical data at an automatically-selected display resolution, the method comprising:

(a) automatically analyzing medical data;

(b) automatically selecting a display resolution for the medical data based on the analysis in (a); and (c) displaying the medical data with the display resolution automatically selected in (b);

wherein (a) comprises comparing at least a portion of the medical data at a plurality of display resolutions to a criterion, and wherein (b) comprises selecting a display resolution from the plurality of display resolutions that results in the at least a portion of the medical data best fitting the criterion.

2. The method of claim 1, wherein (a) comprises calculating a plurality of screen areas occupied by the medical data at a respective plurality of display resolutions, and wherein (b) comprises selecting the display resolution that results in a largest occupied screen area.

3. The method of claim 1, wherein (a) comprises calculating a plurality of screen areas occupied by the medical data at a respective plurality of display resolutions, and wherein (b) comprises selecting the display resolution that results in a smallest occupied screen area.

4. The method of claim 1, wherein (a) comprises determining that the medical data comprises a medical report, and wherein (b) comprises selecting a display resolution that is predetermined for a medical report.

5. The method of claim 1, wherein (a) comprises determining an identifier associated with the medical data, and wherein (b) comprises selecting a display resolution that is predetermined for the identifier.

6. The method of claim 5, wherein the identifier identifies a medical data acquisition device.

7. The method of claim 1, wherein the display resolution is automatically selected in (b) using a look-up table.

8. The method of claim 1 further comprising scaling the medical data.

9. The method of claim 1, wherein the medical data comprises a medical image.

10. The method of claim 1, wherein the medical data comprises a diagnostic medical ultrasound image.

11. The method of claim 1, wherein the medical data comprises a medical report.

12. A method for displaying medical data at an automatically-selected display resolution, the method comprising:

(a) displaying a plurality of medical images on a first display device;

(b) automatically analyzing a medical image selected from the plurality of medical images;

(c) automatically selecting a display resolution for the selected medical image based on the analysis in (b); and (d) displaying the selected medical image with the display resolution automatically selected in (c) on a second display device.

13. The method of claim 13, wherein (b) comprises comparing at least a portion of the selected medical image at a plurality of display resolutions to a criterion, and wherein (c) comprises selecting a display resolution from the plurality of display resolutions that results in the at least a portion of the medical image best fitting the criterion.

14. The method of claim 12, wherein (b) comprises calculating a plurality of screen areas occupied by the medical image at a respective plurality of display resolutions, and wherein (c) comprises selecting the display resolution that results in a largest occupied screen area.

15. The method of claim 12, further comprising scaling the medical image.

16. The method of claim 12, wherein the medical image comprises a diagnostic medical ultrasound image.

17. A diagnostic medical data review system comprising a display device; and a processor operative to automatically select a display resolution for medical data based on an analysis of the medical data, and operative to display the medical data with the automatically-selected display resolution;

wherein the processor is operative to compare at least a portion of the medical data at a plurality of display resolutions to a criterion, and operative to select a display resolution from the plurality of display resolutions that results in the at least a portion of the medical data best fitting the criterion.

18. The invention of claim 17, wherein the processor is operative to determine that the medical data comprises a medical report, and is operative to select a display resolution that is predetermined for a medical report.

19. The invention of claim 17, wherein the processor is operative to determine an identifier associated with the medical data, and is operative to select a display resolution that is predetermined for the identifier.

20. The invention of claim 17, wherein the processor is operative to scale the medical data.

21. The invention of claim 17, wherein the medical data comprises a medical image.

22. The invention of claim 17, wherein the medical data comprises a diagnostic medical ultrasound image.

23. The invention of claim 17, wherein the medical data comprises a medical report.

24. A method for displaying medical data at an automatically-selected display resolution, the method comprising:

(a) automatically analyzing medical data;

(b) automatically selecting a display resolution for the medical data based on the analysis in (a); and (c) displaying the medical data with the display resolution automatically selected in (b);

wherein (a) comprises determining that the medical data comprises a medical report, and wherein (b) comprises selecting a display resolution that is predetermined for a medical report.

25. A method for displaying medical data at an automatically-selected display resolution, the method comprising:

(a) automatically analyzing medical data;

(b) automatically selecting a display resolution for the medical data based on the analysis in (a); and (c) displaying the medical data with the display resolution automatically selected in (b);

wherein (a) comprises determining an identifier associated with the medical data, and wherein (b) comprises selecting a display resolution that is predetermined for the identifier.

26. The method of claim 25, wherein the identifier identifies a medical data acquisition device.

27. A diagnostic medical data review system comprising a display device; and a processor operative to automatically select a display resolution for medical data based on an analysis of the medical data, and operative to display the medical data with the automatically-selected display resolution;

wherein the processor is operative to determine that the medical data comprises a medical report, and is operative to select a display resolution that is predetermined for a medical report.

28. A diagnostic medical data review system comprising
a display device; and
a processor operative to automatically select a display resolution for medical data based on an analysis of the medical data, and operative to display the medical data with the automatically-selected display resolution; wherein the processor is operative to determine an identifier associated with the medical data, and is operative to select a display resolution that is predetermined for the identifier.

* * * * *